United States Patent
Baum

(10) Patent No.: US 6,186,143 B1
(45) Date of Patent: *Feb. 13, 2001

(54) APPARATUS FOR SUPPLYING ATMOSPHERIC AIR AND AT LEAST ONE ADDITIONAL GAS TO A RESPIRATING SUBJECT

(75) Inventor: Marcel Baum, Bernstein (AT)

(73) Assignee: Siemens Elma AB, Solna (SE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/867,943

(22) Filed: Jun. 3, 1997

(30) Foreign Application Priority Data

Jun. 19, 1996 (SE) .................................. 9602415

(51) Int. Cl.[7] ....................................... A62B 7/00
(52) U.S. Cl. .......................... 128/205.11; 128/203.25; 128/203.14
(58) Field of Search .................. 128/204.18, 205.11, 128/200.92, 203.12, 203.14, 203.25

(56) References Cited

U.S. PATENT DOCUMENTS

| | | | |
|---|---|---|---|
| 3,669,134 | * 6/1972 | Dobritz | 128/205.11 |
| 3,830,257 | * 8/1974 | Metivier | 128/205.11 |
| 3,848,617 | * 11/1974 | Dray | 128/205.11 |
| 4,072,148 | * 2/1978 | Munson et al. | 128/205.11 |
| 4,819,629 | * 4/1989 | Jonson | 128/200.14 |
| 4,984,158 | * 1/1991 | Hillsman | 128/203.12 |
| 5,383,449 | * 1/1995 | Forare et al. | 128/205.11 |
| 5,497,765 | * 3/1996 | Praud et al. | 128/203.25 |
| 5,615,669 | * 4/1997 | Olsson et al. | 128/203.25 |
| 5,755,221 | * 5/1998 | Bisgaard | 128/200.22 |
| 5,845,633 | * 12/1998 | Psaros | 128/203.25 |

FOREIGN PATENT DOCUMENTS

| | | |
|---|---|---|
| AS 1 233 537 | 2/1967 | (DE) . |
| 2 200 167 | 7/1988 | (GB) . |
| WO 92/06730 | 4/1992 | (WO) . |
| WO 96/24402 | 8/1996 | (WO) . |

* cited by examiner

*Primary Examiner*—Aaron J. Lewis
(74) *Attorney, Agent, or Firm*—Hill & Simpson

(57) ABSTRACT

An apparatus for supplying air and at least one additional gas to a respirating subject has a container with an open end for receiving air, which is connected to a tubing system for conveying gas to the subject. The additional gas is supplied from an additional gas source via a metering system and a supply line to the container. As gas is supplied to the subject during inspiration phases by a compressor, air will flow into the container via the open end. At the same time a flow of additional gas is supplied to the container via a point of entry. During expiration phases gas will be diverted via a flow divider to flow back to the container via the supply line for the additional gas. A homogeneous and controllable concentration of additional gas is obtained within the container before each inspiration phase. The apparatus requires only a few components, making it a low cost apparatus, but it provides a good control of the concentration of additional gas supplied to the patient.

12 Claims, 2 Drawing Sheets

APPARATUS FOR SUPPLYING ATMOSPHERIC AIR AND AT LEAST ONE ADDITIONAL GAS TO A RESPIRATING SUBJECT

BACKGROUND OF THE INVENTION

1. Field of the Invention

The present invention relates to an apparatus for supplying air and at least one additional gas to a respirating subject during inspiration phases, of the type having a container which is open to surrounding atmosphere at one end for receiving air, a tubing system connected to the other end of the container and connectible to the subject, a source of an additional gas and a point of entry for the additional gas to mix with the air to be supplied to the subject.

2. Description of the Prior Art

Advanced ventilators (respirators), capable of providing a number of different respiration modes, are usually complex to use and also expensive. Normally, they also require reliable power sources and are quite heavy. Together this makes it difficult to use this kind of ventilator in home care equipment or as resuscitation aid for ambulances, air craft and similar locations. Such equipment preferably should be easy to use and at the same time be reliable.

A reliable light weight and low cost ventilator is therefore desirable. Such an apparatus should be able to provide atmospheric air and at least one additional gas, such as oxygen.

An apparatus of this kind is described in German OS 1 233 537. The apparatus disclosed therein has a container having an open end toward ambient air and a connection to a tubing system leading to a patient at the other end. Between the container and the patient an additional gas such as oxygen can be provided.

The additional gas is supplied in a continuous flow. During spontaneous inhalation the patient will draw gas from the container, which then is mixed with the additional gas. During expiration the additional gas will flow toward the container (which is open to ambient atmosphere and thus is unable to generate an overpressure preventing the gas to flow through it in both directions). Due to the continuous supply of oxygen, the first part of the gas supplied to the patient during the initial part of inhalation will be highly enriched with additional gas and may even be comprised almost entirely of the additional gas.

Depending on the tidal volume inspired by the patient, the amount of the additional gas will be reduced during the remaining part of the inhalation. The reduction will depend on the flow of air from the container and the flow of the supplied additional gas. The respiratory gas flow is normally irregular during an inhalation and the concentration of the additional gas over the entire inhalation phase will thus vary to a high degree. The manner of breathing (few deep breaths or many shallow breaths) will determine the minute volume of the additional gas inhaled by the patient.

It is therefore desirable to be able to supply a gas having a homogeneous mixture of air and the additional gas and it is also desirable to be able to select a specific concentration of the additional gas.

The advanced ventilators referred to above usually have servo controlled valves which can respond quickly and accurately for providing exact mixtures of different gases. It would thus be possible to include an advanced servo controlled valve or similar and a flow meter between the container and the patient in the described known apparatus. By measuring the flow of air to the patient the valve could be controlled to supply an amount of additional gas based on the measured flow, which would result in a desired concentration of additional gas in the air. Since the flow may vary significantly during an inspiration, however, and may momentarily reach flow values of several liters per second, the valve must be both very fast and very accurate in order to supply the required amount of additional gas. Although such valves do exist, they are usually very expensive, require a relatively complex regulation circuit and are also more power demanding than other valves. Further, they usually also require that the additional gas be taken from a high pressure source in order to operate satisfactorily.

SUMMARY OF THE INVENTION

It is an object of the present invention to provide an apparatus of the type initially described which can provide a homogeneous gas mixture containing a defined amount of an additional gas to a patient in a simple but reliable and stable fashion.

The object is achieved in accordance with the invention in an apparatus of the type initially described, having the point of entry for the additional gas located between the connection of the tubing system at the other end of the container and the open end in the container, and a metering system which supplies the additional gas from the source of additional gas so that a predetermined concentration of additional gas is obtained in the gas between the point of entry and the tubing system before the onset of each inspiration phase.

Supplying the additional gas directly to the container, instead of between the container and the patient, provides a system where the air and the additional gas may mix and produce an evenly mixed gas, even though the air is entering the container with a variable flow. The additional gas can be supplied in a constant flow rate based on a required minute volume and desired concentration of the additional gas in air to be supplied to the patient.

In one embodiment of the apparatus of the invention, the volume between the point of entry of the additional gas and the patient corresponds to at least one tidal volume for the subject. This allows the gas mixture for the next inhalation to be prepared either during the ongoing inspiration or during the intervening expiration phase.

In another embodiment of the apparatus of the invention, an arrangement for generating a flow of mixed air and additional gas from the container to the subject is arranged somewhere along the tubing system. This is advantageous for patients who are unable to or have difficulties in breathing sufficient amounts of gas themselves.

In another embodiment of the apparatus of the invention the metering system supplies the additional gas at a constant rate via a supply line and a feedback connection is arranged between the tubing system and the supply line. A flow divider is arranged for diverting a flow of air and additional gas to the subject during inspiration phases and for diverting the flow of air and additional gas to the feedback connection during expiration phases for conveying the air and the additional gas back to the container. If a constant flow is generated in the tubing system, the flow divider can, during inspiration, divert a first variable flow toward the subject and a second variable flow to the feedback connection. The sum of the two flows is equal to the constant flow. During expiration, the entire flow is normally diverted to the feedback connection. This arrangement enhances the mixing of the additional gas and air and improves the homogeneity of the gas mixture to be supplied to the patient.

It is advantageous to arrange a flow meter to measure the flow of air and additional gas to the subject. Control over different parts of the apparatus may be utilized with relatively simple regulation components based on the measured flow.

DESCRIPTION OF THE DRAWINGS

FIG. 3 is an excerpt from FIG. 2, showing a variation of the second embodiment.

DESCRIPTION OF THE PREFERRED EMBODIMENTS

Figure 1:
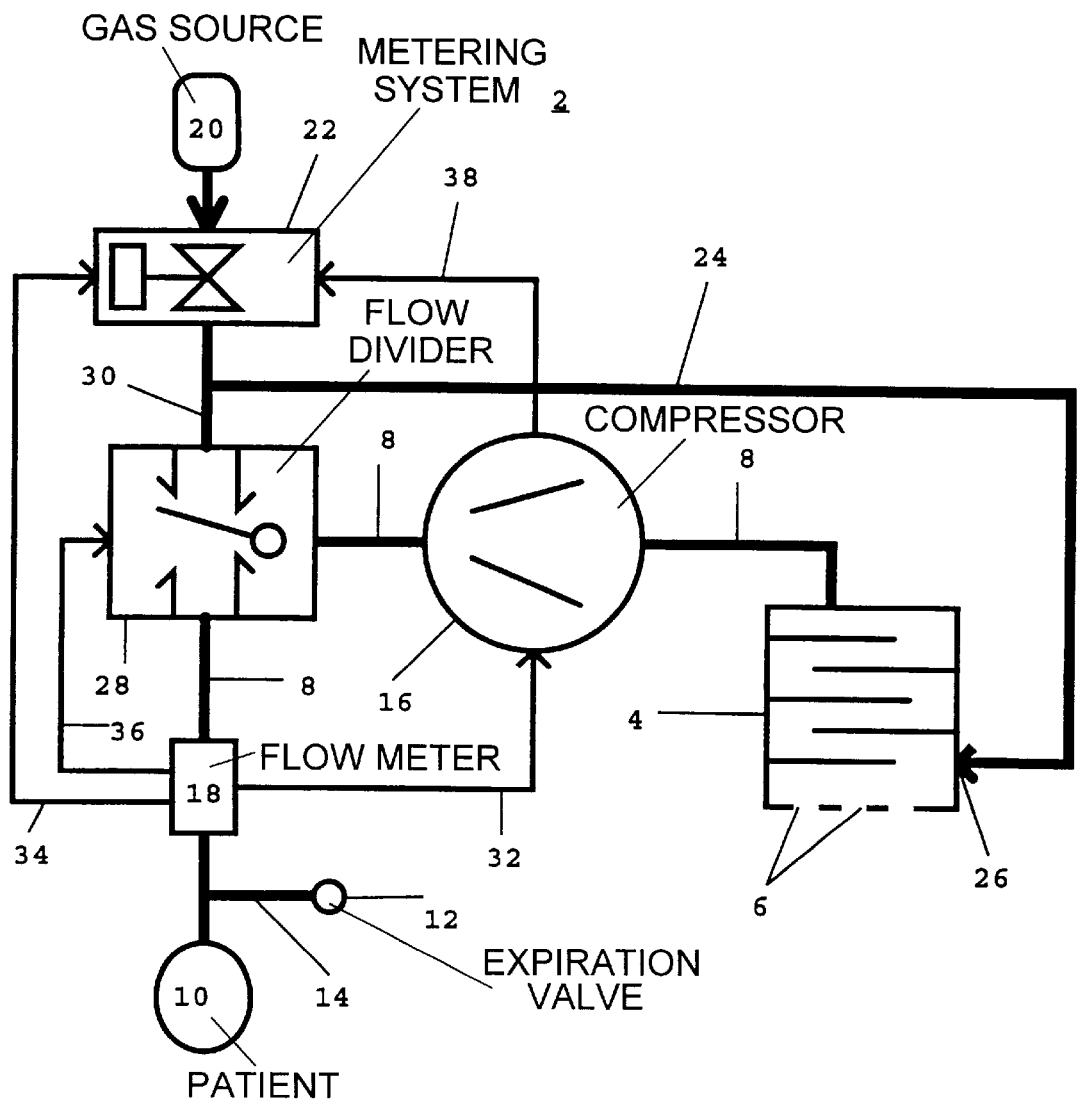
FIG. 1 shows a first embodiment of the apparatus of the invention.

A first embodiment of the apparatus according to the invention is designated 2 and is shown in FIG. 1. The apparatus 2 has a container 4 which is open in one end 6 to the surrounding atmosphere. The container 4 preferably has a labyrinthine interior for improving the mixing of gases flowing through it. A tubing system 8 is connected to the other end of the container 4 and conveys a respiratory gas from the container 4 to a patient 10. An expiration valve 12 is connected to an exhalation tube 14 to allow gas to flow from the patient 10 during exhalation.

A compressor 16 is arranged in the tubing system 8 for generating a flow of gas toward the patient 10 during inspiration. A significant breathing support and even breathing control is thereby obtained. The compressor 16 can generate a constant or a variable flow of gas. The compressor 16 can also be replaced by a fan or a pump.

The flow of gas supplied to the patient 10 is measured in a flow meter 18, located in the tubing system 8 near the patient 10.

An additional gas to be supplied to the patient 10 is stored in a gas source 20. The additional gas is supplied to the container 4 via a metering system 22 and a supply line 24. A point of entry 26 for the additional gas into the container 4 is arranged between the open end 6 of the container 4 and the tubing system 8. The additional gas is mixed with air in the container 4 for forming the respiratory gas.

The volume between the point of entry 26 and the patient 10 should be at least one tidal volume for the patient 10. Preferably, the volume between the point of entry 26 and the compressor 16 (or flow divider 28) has this volume.

A flow divider 28 is also arranged in the tubing system 8. The flow divider 28 can be operated to lead a flow of gas in two directions. A flow of respiratory gas can be diverted to the patient 10 and to the supply line 24 via a feedback connection 30. The gas flow rom the compressor 16 can be partially or completely diverted to either of the two directions.

The operation of the apparatus 2 can be described most easily if the compressor 16 is regarded as a constant flow generator of gas, which operates continuously over both inspiration and expiration phases. During inspiration the flow divider 28 is operated to divert a flow of respiratory gas to the patient 10 via the flow meter 18. A variable flow can be generated by varying the proportions of gas flows diverted in the two directions. The flow generated by the compressor 16 should in this case correspond to the highest flow required for the patient 10. At the same time a continuous flow of the additional gas, for instance oxygen, is supplied to the supply line 24 via the metering system 22 and is fed to the container 4, which the additional gas enters near the open end 6. Simultaneously, air will enter the container 4 via the open end 6. Basically, the same flow which is conducted from the container 4 via the tubing system 8 to the patient 10 will enter the container as the sum of the flow of air via the open end 6 and the flow of additional gas (or mixture of air and additional gas) via the point of entry 26.

When the expiration phase commences, the flow divider 28 is changed to divert the entire gas flow via the feedback connection 30 to the supply line 24. The additional gas is still supplied via the metering system 22 with a continuous flow rate and thereby mixes with the gas from the tubing system 8. This gas is made up of air and additional gas, but is not mixed in the desired proportions. As it flows through the supply line 24, it will be enriched with more additional gas and further mixed. This new mixture will enter the container 4.

Depending on the volume in the feedback connection 30 and the supply line 24, the gas will circulate one or more times through the system during the expiration phase. The volumes of the tubing system 8, container 4, supply line 24 and the feedback connection 30 as well as the constant flow of the additional gas are selected such that the volume of gas between the point of entry 26 and the compressor 16 (or flow divider 28 or patient 10) is filled with the respiratory gas (i. e. the desired mixture of air and additional gas).

During expiration, the flow of gas entering the container 4 at the point of entry 26 via the supply line 24 will be somewhat larger than the flow leaving the container 4 via the tubing system 8 (i. e. the flow generated by the compressor 16) due to addition of the constant flow of additional gas in the supply line 24. Therefore, no air will enter the container 4 via the open end 6. By selecting the volume between the open end 6 and the point of entry 26 in an appropriate manner, the loss of additional gas to the surrounding atmosphere can be minimized, even at high levels of concentration of the additional gas, i. e. at relatively high constant flows of the additional gas.

The constant flow of the additional gas is selected based on the desired concentration of the additional gas and the total minute volume of respiratory gas to be supplied to the patient. If the required minute volume is 10 liters and the respiratory gas is to contain 10% of additional gas, 1 liter of additional gas should be supplied each minute. Hence, the constant flow of additional gas corresponds to the required minute volume of the additional gas, in other words 1 liter/minute. Since no additional gas will escape from the system and the supplied minute volume can be controlled via the flow meter and the compressor, the apparatus will operate in a very satisfactory manner.

It should be noted that for many additional gases, such as oxygen, nitrous oxide or similar, a variance in the selected concentration of ±1–2% (i. e. with a selected concentration of 10% additional gas, the mixture supplied to the patient can contain 8–12%) is not serious for this kind of apparatus 2.

The control of the compressor 16 is indicated by a control line 32 from the flow meter 18. The compressor 16 (or a similar flow generating device) can thus be operated to supply a variable flow to the patient 10. The operation of the apparatus 2 is basically the same even if a variable flow is used. The difference is that the flow of air entering the container 4 will vary more. The feedback system of air and additional gas will, however, ensure that a homogeneous and desired mixture is obtained.

As stated above, the variable flow can also be achieved by means of the flow divider 28. With a variable flow generated by the compressor 16, however, the flow divider 28 can operate as (or even be replaced with) a switch and divert the entire gas flow either to the patient 10 or to the feedback connection 30.

It is also possible to use a switch instead of the flow divider 28 when a constant flow of gas is generated by the compressor 16.

It is not even necessary to supply a continuous flow of the additional gas. It is sufficient to supply the required minute volume only. This can therefore be supplied with a variable flow to further enhance the mixing of the gases, such that a higher flow of additional gas is supplied during the inspiration phases, when a higher flow of air from the surrounding atmosphere may enter the container 4 via the open end 6 and a reduced flow of additional gas is supplied during the expiration phases. This is suitable when the mixture of air and additional gas in the container 4 only needs to be further enriched with the additional gas for obtaining the final mixture to be supplied to the patient 10.

Other controls in the apparatus 2 can be exercised based on measured flow. For instance, the metering system 22 can be controlled based on the measured flow via a control line 34 and the flow divider 28 may also be controlled based on the flow measured by flow meter 18, indicated by a control line 36.

The flow meter 18 in these instances has the required regulation components. Since regulation can be based on known regulation systems, these need not be further described herein.

The supply of the additional gas may also be controlled via the compressor 16 directly, as indicated by control line 38.

Figure 2:
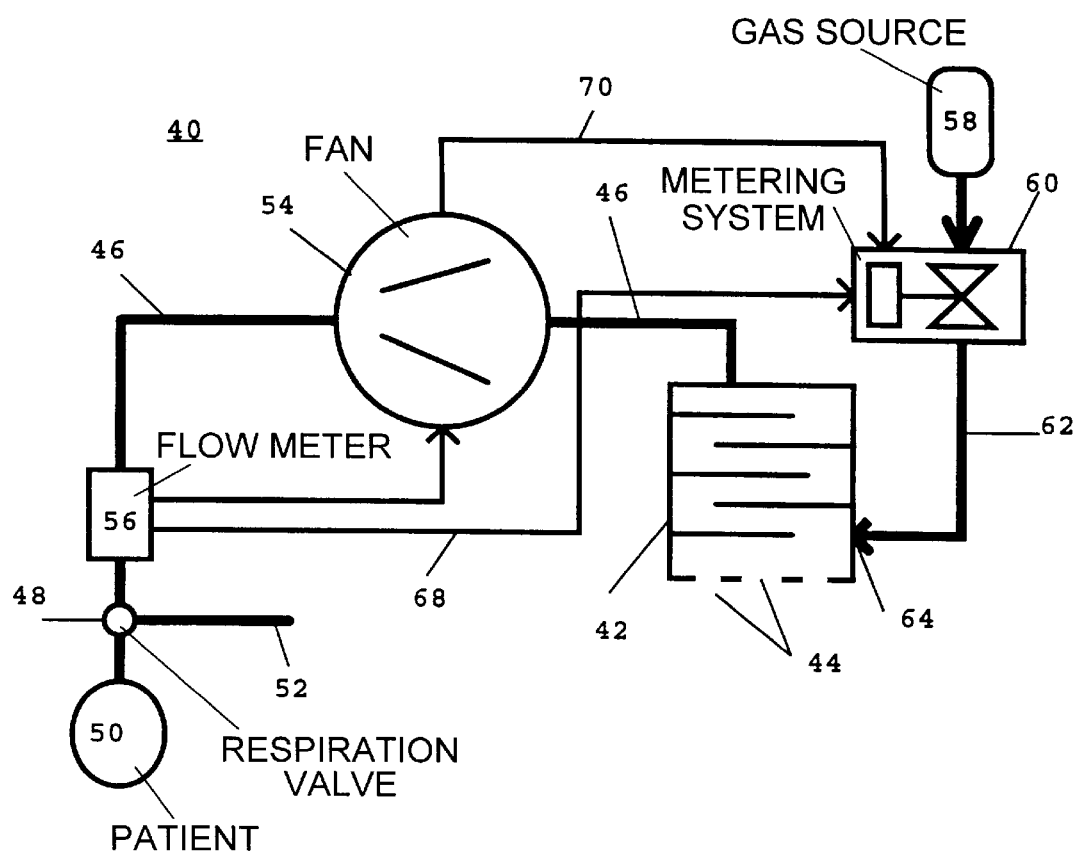
FIG. 2 shows a second embodiment of the apparatus of the invention.

In FIG. 2 a second embodiment of the apparatus is shown and designated 40. The apparatus 40 has a container 42 with an open end 44, a tubing system 46, a respiration valve 48, via which the respiratory gas is supplied to the patient 50, an exhalation tube 52, a fan 54, a flow meter 56, a source of additional gas 58, a metering system 60, a supply line 62 and a point of entry 64 for the additional gas into the container 42.

The apparatus 40 operates in a somewhat different manner from the apparatus 2 in FIG. 1. Basically, the apparatus 40 only operates during inspiration phases, during which the fan 54 is activated to generate a flow of gas toward the patient 50. At the same time, the metering system 60 is controlled to supply a flow of additional gas via the supply line 62 and the point of entry 64. Simultaneously, air will enter the container 42 via the open end 44.

Again, the operation of the apparatus 40 will be described initially when a constant gas flow of respiratory gas is generated by the fan 54. In this case the metering system 60 need only supply a continuous flow of gas based on the selected concentration of additional gas and tidal volume of respiratory gas. The volume of additional gas to be mixed with air from the surrounding atmosphere during each inspiration phase can hereby be calculated. The flow of mixed respiratory gas conveyed from the container 42 into the tubing system 46 will correspond to the sum of the air flow entering the container 42 via the open end 44 and the constant flow of gas entering the container 42 via the point of entry 64. A homogeneous gas mixture will thus be provided and prepared for the next inspiration phase. During the expiration phase the entire system may be in a resting mode; it is not even necessary to disconnect the fan.

If the fan 54 is controlled to provide a variable flow of gas or if the patient 50 is breathing spontaneously, the control needs to be somewhat different in order to ascertain the homogeneous mixture and desired concentration of additional gas in the respiratory gas.

First of all, the volume between the point of entry 64 and the fan 54 should be at least two (preferably three or four) tidal volumes.

As the variable flow of respiratory gas is conveyed from the container 42 via the tubing system 46, a variable flow of air will enter the container 42 at the open end 44. Even so, a constant flow of additional gas may be provided via the point of entry 64. Since the volume above the point of entry 64 comprises several tidal volumes and the container is constructed to enhance turbulence from the gas within the container 42, there will be ample time for the gases to mix and obtain the desired concentration, before being supplied to the patient 50. The container 42 could also contain a more open compartment near its upper end (approximately one tidal volume large), in order to further enhance the mixing.

The metering system 60 may also be controlled to provide a somewhat larger flow at the beginning of inspiration, when the flow leaving the container 42 normally is larger, and reduce the flow during the latter part of the inspiration. This will further enhance and quicken the mixing of the gases, since the flow of air through the open end 44 will also be higher at the beginning of inspiration and lower at the end of inspiration. The measured flow may also be used to control the metering system 60 via a control line 68. Control could be simple, for instance by increasing the constant flow in steps as the measured flow increases, and vice versa.

It should be noted that this kind of control of the metering system 60 in no way corresponds to the servo valve control systems known in the prior art. Such prior art systems require both a very fast and also accurate control of the flow of additional gas for obtaining a desired mixture.

The metering system 60 can also be controlled by the fan 54 as indicated with the control line 70. This is similar to controlling the metering system 60 based on measured flow. When using the system for controlled breathing it may be preferable to use this kind of control since it provides a faster reaction.

The fan 54 itself can be controlled by a feedback system based on the measured flow in the flow meter 56, as indicated with control line 66.

Both embodiments shown in this application can use low pressure gas sources (such as liquid oxygen tanks or oxygen concentrators) for the additional gas. The consumption of the additional gas is minimized and the metering systems can be fairly simple and even slow. The only requirement is that they are exact enough to provide the set flow (within acceptable limits).

Alternative embodiments are also possible, for instance the fan 54 in the second embodiment may be replaced with a compressor or a pump. When a pump is used, it should preferably be a positive displacement pump 55, as shown in FIG. 3. If a compressor is used and is operated constantly during both inspiration and expiration phases, flow dividers or switches should be included in the tubing system 46 for disconnecting the compressor from the container 42 and patient 50 during expiration phases. This can be made by having flow dividers or switches which are connected to ambient atmosphere during expiration, whereby the compressor will only pump air from the atmosphere to the atmosphere during the expiration phases.

The point of entry can basically be located anywhere between the open end of the container and the connection to the tubing system, provided that the volume of gas between the point of entry and the patient (or compressor/fan/pump) comprises at least one tidal volume.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for supplying atmospheric air to a respirating subject, comprising:
    a container having a first end open to ambient atmosphere for receiving atmospheric air into said container, and having a second end;
    means for generating a flow of atmospheric air from said second end of said container;
    a tubing system connected to said means for generating a flow and adapted for connection to a respirating subject;
    a feedback connection between said tubing system and said container; and
    a flow divider for controllably diverting a variable portion of said flow of atmospheric air from said second end of said container to said tubing system and a remaining portion of said flow of atmospheric air from said second end of said container to said feedback connection.

2. An apparatus as claimed in claim 1 wherein said means for generating a flow comprises a compressor.

3. An apparatus as claimed in claim 1 wherein said means for generating a flow comprises a fan.

4. An apparatus as claimed in claim 1 wherein said means for generating a flow comprises a pump.

5. An apparatus as claimed in claim 4 wherein said pump comprises a positive displacement pump.

6. An apparatus as claimed in claim 1 wherein said metering means comprises means for controlling supply of said additional gas for causing said additional gas to be supplied only during each inspiration phase.

7. An apparatus as claimed in claim 1 further comprising a flow meter for measuring a flow of atmospheric air and said additional gas supplied to a respirating subject.

8. An apparatus as claimed in claim 7 wherein said flow meter comprises means for emitting a signal to said metering means corresponding to said flow of atmospheric air and said additional gas measured by said flow meter, and wherein said metering means comprises means for controlling the supply of said additional gas dependent on said signal.

9. An apparatus as claimed in claim 1 further comprising a source of additional gas and a supply line connecting said source of additional gas to a point of entry into said container, between said tubing system and said first end of said container, for mixing said additional gas with atmospheric air for supply to a respirating subject via said tubing system, and a metering unit for controlling supply of said additional gas to supply said additional gas at a constant rate via said supply line.

10. An apparatus for supplying atmospheric air to a respirating subject, comprising:
    a container having a first end open to ambient atmosphere for receiving atmospheric air into said container, and having a second end;
    means for generating a flow of atmospheric air from said second end of said container;
    a tubing system connected to said means for generating a flow and adapted for connection to a respirating subject;
    a feedback connection between said tubing system and said container; and
    a flow divider for diverting a flow of atmospheric air to a respirating subject each inspiration phase and for diverting a flow of atmospheric air to said feedback connection during each expiration phase.

11. An apparatus for supplying atmospheric air and at least one additional gas to a respirating subject, comprising:
    a container having a first end open to ambient atmosphere for receiving atmospheric air into said container, and having a second end;
    means for generating a flow of mixed atmospheric air and said additional gas from said second end of said container;
    a tubing system connected to said second end of said container and adapted for connection to a respirating subject;
    a source of additional gas connected at a point of entry via a supply line for said additional gas for mixing said additional gas with atmospheric air for supply to a respirating subject via said tubing system;
    a metering unit for controlling supply of said additional gas from said source of additional gas to said point of entry for producing a predetermined concentration of said additional gas before each inspiration phase of a respirating subject;
    a feedback connection between said tubing system and said supply line; and
    a flow divider for diverting a flow of atmospheric air to a respirating subject each inspiration phase and for diverting a flow of atmospheric air to said feedback connection during each expiration phase.

12. An apparatus for supplying atmospheric air and at least one additional gas to a respirating subject, comprising:
    a container having a first end open to ambient atmosphere for receiving atmospheric air into said container, and having a second end;
    means for generating a flow of mixed atmospheric air and said additional gas from said second end of said container;
    a tubing system connected to said second end of said container and adapted for connection to a respirating subject;
    a source of additional gas connected at a point of entry via a supply line for said additional gas for mixing said additional gas with atmospheric air for supply to a respirating subject via said tubing system;
    a metering unit for controlling supply of said additional gas from said source of additional gas to said point of entry for producing a predetermined concentration of said additional gas before each inspiration phase of a respirating subject;
    a feedback connection between said tubing system and said supply line; and
    a flow divider for diverting a flow of atmospheric air and said additional gas to a respirating subject each inspiration phase and for diverting a flow of atmospheric air and said additional gas to said feedback connection during each expiration phase.

* * * * *